United States Patent [19]

Engbert et al.

[11] Patent Number: 4,698,424
[45] Date of Patent: Oct. 6, 1987

[54] ISOCYANATO-ISOCYANURATE DERIVATIVES

[75] Inventors: Theodor Engbert, Dormagen; Hartmut Knöfel, Odenthal-Erberich, both of Fed. Rep. of Germany; Gerhard Wegener, New Martinsville, W. Va.

[73] Assignee: Bayer Aktiengesellschaft, Leverkusen, Fed. Rep. of Germany

[21] Appl. No.: 666,586

[22] Filed: Oct. 31, 1984

[30] Foreign Application Priority Data

Nov. 2, 1983 [DE] Fed. Rep. of Germany ....... 3339579

[51] Int. Cl.[4] ............................................ C07D 251/34
[52] U.S. Cl. ................................... 544/222; 524/101; 524/197
[58] Field of Search .............................. 544/222, 193; 260/453 AM

[56] References Cited

U.S. PATENT DOCUMENTS

| | | | |
|---|---|---|---|
| 3,645,979 | 2/1972 | Liebsch et al. | 260/77.5 NC |
| 3,663,514 | 5/1972 | Campbell et al. | 260/453 AM |
| 3,919,218 | 11/1975 | Schmitt et al. | 260/248 NS |
| 4,246,132 | 1/1981 | Gras et al. | 544/222 |
| 4,255,569 | 3/1981 | Müller et al. | 544/222 |
| 4,335,219 | 6/1982 | Clarke et al. | 544/193 |
| 4,379,905 | 4/1983 | Stemmler et al. | 544/222 |
| 4,412,073 | 10/1983 | Robin | 544/193 |
| 4,419,513 | 12/1983 | Breidenbach et al. | 544/222 |
| 4,512,797 | 4/1985 | Parg et al. | 544/222 |
| 4,518,729 | 5/1985 | Breidenbach et al. | 524/101 |
| 4,518,761 | 5/1985 | Richter et al. | 544/193 |

FOREIGN PATENT DOCUMENTS

| | | | |
|---|---|---|---|
| 010589 | 8/1979 | European Pat. Off. | 544/222 |
| 949253 | 2/1964 | United Kingdom | 544/222 |
| 1001746 | 8/1965 | United Kingdom | 544/222 |
| 1458564 | 12/1976 | United Kingdom | 544/222 |

OTHER PUBLICATIONS

E. Windemuth, Neue Entwicklungen auf dem Polyurethan-Gebiet (also condensed translation, two pages, 16 and 17), *Kunststoffe*, vol. 57, (1967) pp. 337-343.

L. Havenith, Rapid-Curing Polyurethane Coatings, *Paint Manufacture*, Dec. (1968), pp. 33-38.

W. Wieczorrek, Neue Rasch Trocknende Polyisocyanate für die Lackindustrie, *Farbe und Lack*, 75, (1969), pp. 318-326.

*Primary Examiner*—Henry R. Jiles
*Assistant Examiner*—J. G. Mullins
*Attorney, Agent, or Firm*—Gene Harsh; Joseph C. Gil; Thomas W. Roy

[57] ABSTRACT

The present invention relates to isocyanato-isocyanurates corresponding to the formula

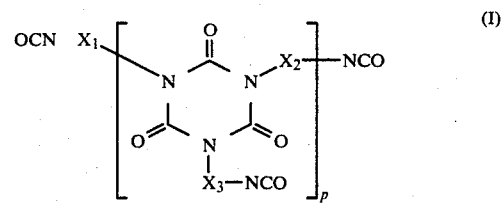

in which $X_1$, $X_2$ and $X_3$ may be the same or different and represent radicals corresponding to the formula

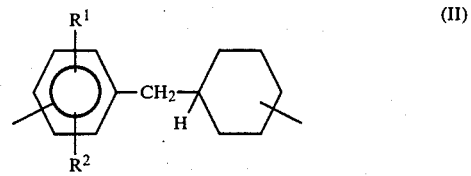

wherein $R^1$ and $R^2$ may be the same or different and represent hydrogen or $C_1$–$C_{12}$ alkyl groups, and p is a whole or (on a statistical average) fractional number of from 1 to 5.

The present invention also relates to a process for producing these isocyanato-isocyanurates and additionally relates to the use of the new isocyanato-isocyanurates, optionally blocked by blocking agents for isocyanate groups, as the isocyanate component in the produciton of isocyanate polyaddition products, preferably polyurethane lacquers.

3 Claims, No Drawings

ISOCYANATO-ISOCYANURATE DERIVATIVES

BACKGROUND OF THE INVENTION

1. Field of the Invention

This invention relates to new isocyanato-isocyanurates based on isocyanatobenzyl cyclohexyl isocyanates optionally alkyl-substituted on the aromatic ring, to a process for their production by partial trimerization of these diisocyanates and to the use of the isocyanato-isocyanurates in optionally blocked form as the isocyanate component in the production of isocyanate polyaddition products, preferably polyurethane lacquers.

2. Description of the Prior Art

It is known that isocyanuric acid derivatives can be produced by the catalytic trimerization of organic isocyanates. The trimerization of organic diisocyanates containing isocyanate groups of identical or similar reactivity only gives triisocyanates to a predominant extent when the formation of relatively high molecular weight products is avoided or suppressed by premature termination of the reaction.

For the production of monomer-free isocyanato-isocyanurates (which are of interest as soluble, polyfunctional and, by virtue of their high vapor pressure, as physiologically acceptable isocyanates, particularly for lacquer applications), the monomeric diisocyanate has to be removed from these isocyanurate-containing products obtained by partial trimerization in a second process step, for example by thin-layer distillation.

By contrast, diisocyanates containing two isocyanate groups of different reactivity may, in certain cases, be directly reacted in a single step to form soluble isocyanato-isocyanurates. Examples of selective trimerization reactions such as these can be found in British patent No. 949,253 and in DE-AS No. 1,203,792. In these processes, 2,4-tolylene diisocyanate is used as the starting material and is trimerized either in the absence of solvents or in solution to form. isocyanato-isocyanurates. The direct reaction to form low-monomer, sufficiently thin-flowing products is only possible in solution using at least 50% by weight of solvent. As explained by E. Windemuth (Kunststoffe, Vol. 57, 1967, pages 337–343), the trimerization of 2,4-tolylene diisocyanate normally gives products of very high molecular weight providing the reaction time is sufficiently long: low-monomer products predominantly containing triisocyanates only being obtainable where special trimerization catalysts are used. Isocyanato-isocyanurates containing aromatically bound isocyanate groups are not really suitable for light-stable lacquer systems because products such as these have a tendency towards yellowing.

Mixed isocyanato-isocyanurates produced from aliphatic and aromatic diisocyanates, as described for example by L. Havenith (Paint Manufacture 38, 1968, page 33) and W. Wieczorreck (Farbe und Lack 75, 1969, page 318), turn yellow distinctly more slowly. These polyisocyanates based, for example, on tolylene diisocyanate and 1,6-hexamethylene diisocyanate may be processed to form films having relatively short drying times, so that lacquering can be carried out on the assembly-line principle with short cycle times, as in the case of the purely aromatic isocyanato-isocyanurates. However, the production of mixed isocyanato-isocyanurates containing free aromatic and aliphatic isocyanate groups involves several stages, as described in DE-PS No. 1,670,667.

Lacquer systems based solely on aliphatic isocyanates show extremely high light stability. Corresponding isocyanato-isocyanurates, which are widely used as light-stable surface lacquers in either solvent-free or solvent-containing form, may be produced from 1,6-diisocyanatohexane and from 1-isocyanato3,3,5-trimethyl-5-isocyanatomethyl cyclohexane (isophorone diisocyanate), for example by the processes described in EP No. 0,010,589 and in DE-PS No. 2,325,826, respectively.

Another criterion for the suitability of polyisocyanates for use as isocyanate component in polyurethane lacquers is their compatibility with apolar solvents, for example aromatic and aliphatic hydrocarbons. Isocyanato-isocyanurates produced in particular from aromatic diisocyanates, for example tolylene diisocyanate, show distinct disadvantages in this respect because they can only be diluted to a limited extent with aromatic and aliphatic hydrocarbons.

In DE-OS No. 2,414,413, it is recommended that the polyisocyanate component be additionally modified with fatty alcohols to improve its compatibility with apolar solvents and to reduce its content of unreacted starting diisocyanate. Although this modification does produce a significant improvement in solvent compatibility, it is attended by the disadvantage that isocyanate groups are additionally consumed and are therefore no longer available for the formation of crosslinking sites, thereby reducing the functionality of the polyisocyanates.

The object of the present invention is to provide new isocyanato-isocyanurates which can be inexpensively produced by a technically simple process and which show good to very good lacquer properties or property combinations.

This object is achieved by the provision of the new isocyanato-isocyanurates described in detail hereinafter and by the process for their production.

By virtue of the process according to the invention, it is possible in a single step to produce low-monomer isocyanato-isocyanurates which contain almost exclusively aliphatically bound isocyanate groups and, accordingly, give lacquer films characterized by high light stability. In addition, it is also possible by the process according to the invention to produce in a technically simple manner low-monomer isocyanato-isocyanurates of the type which contain both aliphatically and also aromatically bound isocyanate groups and which, accordingly, may be used as lacquer-grade polyisocyanates having graduated reactivity and improved light stability. In addition, some of the products obtained by the process according to the invention show outstanding compatibility with apolar solvents.

SUMMARY OF THE INVENTION

The present invention relates to isocyanato-isocyanurates corresponding to the formula

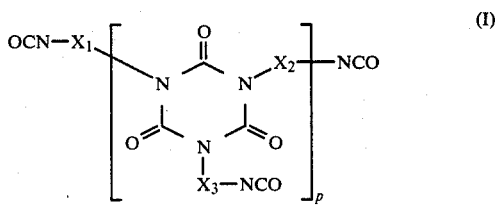

in which $X_1$, $X_2$ and $X_3$ may be the same or different and represent radicals corresponding to the formula

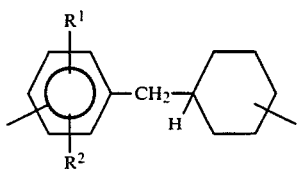 (II)

wherein $R^1$ and $R^2$ may be the same or different and represent hydrogen or $C_1$–$C_{12}$ alkyl groups, and p is a whole or (on a statistical average) fractional number of from 1 to 5.

The present invention also relates to a process for producing these isocyanato-isocyanurates which is characterized in that diisocyanates corresponding to the following formula

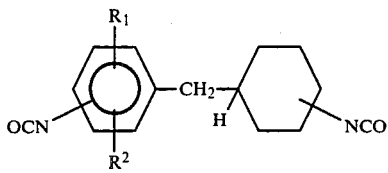 (III)

in which $R^1$ and $R^2$ have the meanings defined in claim 1, are partially trimerized in the presence of catalysts which accelerate the trimerization of isocyanate groups and any excess starting diisocyanates left after the trimerization reaction is removed from the reaction mixture by distillation.

Finally, the present invention also relates to the use of the new isocyanato-isocyanurates, optionally blocked by blocking agents for isocyanate groups, as the isocyanate component in the production of isocyanate polyaddition products, preferably polyurethane lacquers.

DETAILED DESCRIPTION OF THE INVENTION

The isocyanato-isocyanurates according to the invention are often isomer mixtures, particularly where isomer mixtures of diisocyanates are used for their production. In addition, the new isocyanato-isocyanurates, like most conventional isocyanato-isocyanurates, represent homolog mixtures, i.e. they generally represent mixtures of individual isocyanato-isocyanurates corresponding to general formula (I), in which p is a number of from 1 to 5, preferably from 1 to 3, so that the average value of p is also a fractional number within the range from 1 to 5, preferably from 1 to 3 and, more preferably, from 1 to 2. In addition, non-linear, i.e. branched and/or 3-dimensionally crosslinked products are often formed in addition to the polyisocyanates corresponding to general formula (I) in the process according to the invention, which is attributable to the fact that simple triisocyanato-isocyanurate (p=1) is able to further react not only to form linear reaction products (p=2-5), but also to form branched, 2-dimensional and also crosslinked, 3-dimensional polyisocyanato-polyisocyanurates. Non-linear, relatively high molecular weight homologs such as these may be formed in a proportion of up to about 50% by weight, based on the mixture of isocyanato-isocyanurates as a whole. However, their content preferably amounts to between 0 and about 10% by weight Starting materials for the production of the isocyanato-isocyanurates according to the invention are diisocyanates corresponding to the following general formula

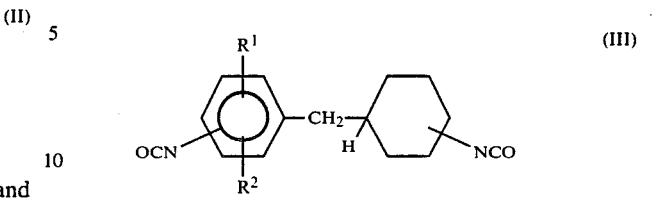 (III)

in which $R^1$ and $R^2$ are as already defined and preferably represent hydrogen or $C_1$–$C_3$ alkyl radicals.

Particularly preferred diisocyanates are those corresponding to formula (III) in which
$R^1$ represents hydrogen and
$R^2$ represents a $C_1$–$C_3$ alkyl radical, more particularly a methyl radical.

Suitable starting isocyanates such as these are, for example, unsubstituted (isocyanatobenzyl)-cyclohexyl isocyanates such as, for example, 1-(4'-isocyanatobenzyl)-4-isocyanatocyclohexane, 1-(2'-isocyanatobenzyl)-4-isocyanatocyclohexane, 1-(4'-isocyanatobenzyl)-2-isocyanatocyclohexane; (alkyl-isocyanatobenzyl)-cyclohexyl isocyanates, such as 1-(3'-methyl-4'-isocyanatobenzyl)-4-isocyanatocyclohexane, 1-(3'-isocyanato-4'-methylbenzyl)-4-2-isocyanatocyclohexane, 1-(3'-methyl-4'-isocyanatobenzyl)-1-(2'-methyl-5'-isocyanatobenzyl)-4-isocyanatocyclohexa 1-(2'-isocyanato-4'-methylbenzyl)-4-isocyanatocyclohexane, 1-(3'-methyl-5'-isocyanatobenzyl)-4-isocyanatocyclohexane, 1-(3'-methyl-5'-isocyanatobenzyl)-2-isocyanatocyclohexane, 1-(3'-ethyl-4'-isocyanatobenzyl)-4-isocyanatocyclohexane, 1-(3'-isocyanato-4'-ethylbenzyl)-2-isocyanatocyclohexane, 1-(2'-isocyanato-3'-ethylbenzyl)-4-isocyanatocyclohexane, 1-(3'-isopropyl-4'-isocyanatobenzyl)-4-isocyanatocyclohexane, 1-(2'-isocyanato-4'-tert.-butyl)-4-isocyanatocyclohexane, 1-(3'-isocyanato-4'-dodecylbenzyl)-4-isocyanatocyclohexane; (dialkyl-isocyanatobenzyl)-cyclohexyl isocyanates, such as 1-(3',5'-dimethyl-4'-isocyanatobenzyl)-4-isocyanatocyclohexane, 1-(3',5'-dimethyl-4'-isocyanatobenzyl)-2-isocyanatocyclohexane, 1-(2',6'-dimethyl-4'-isocyanatobenzyl)-4-isocyanatocyclohexane, 1-(3'-4'-isocyanato-5'-ethylbenzyl)-2-isocyanatocyclohexane, 1-(3'-methyl-4'-isocyanato-5'-isopropylbenzyl)-4-isocyanatocyclohexane, 1-(2'-isocyanato-3',4'-dimethylbenzyl)4'-isocyanatocyclohexane, 1-(2',5'-dimethyl-4'-isocyanatobenzyl)-4'-isocyanatocyclohexane, 1-(2',5'-dimethyl-6'-isocyanatobenzyl)-4-isocyanatocyclohexane, 1-(3',5'-diethyl-4'-isocyanatobenzyl)-4-isocyanatocyclohexane, 1-(3',5'-diispropyl-4'-isocyanatobenzyl)-4-isocyanatocyclohexane, 1-(3',5'-diisopropyl-4'-isocyanatobenzyl)-2-isocyanatocyclohexane or 1-(3',5'-didodecyl-4'-isocyanatobenzyl)-2-isocyanatocyclohexane.

Also suitable as starting materials are, of course, the other diisocyanates corresponding to general formula (III) and also mixtures of the diisocyanates mentioned by way of example. So far as the suitability of the diisocyanates for use in the process according to the invention is concerned, it is immaterial whether the starting diisocyanates are present in the cis-configuration or in the trans-configuration.

Preferred starting materials for use in the production of the isocyanato-isocyanurates according to the invention are diisocyanates corresponding to general formula (III), of the type obtainable from the diaminoalkyl diphenyl methanes described in EP-A-0,024,665 and in EP-A-0,046,556 by partial nucleus hydrogenation, followed by phosgenation, using the processes described in DE-OS No. 3,245,321 and in DE-OS No. 3,245,320, or mixtures of those diisocyanates.

Starting materials obtainable by these processes, which are preferably used in accordance with the invention, are, for example, isomer mixtures corresponding to general formula (III), of which more than about 70% by weight are diisocyanates corresponding to the following formula

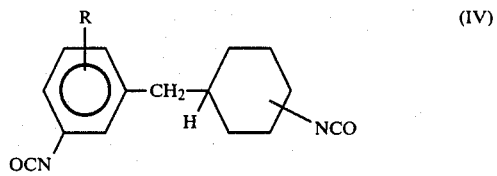

(IV)

In these isomer mixtures, in which R preferably represents short-chain alkyl groups containing from 1 to 3 carbon atoms, more preferably methyl groups, the aliphatically bound isocyanate groups are predominantly in the 2- or 4-position while the radicals R are predominantly in the 2'-, 4'- or 6'-position.

In addition, an isomer mixture corresponding to general formula (III), which almost exclusively contains diisocyanates corresponding to the following formula

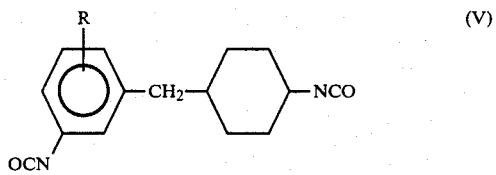

(V)

in which about 70 to 90% of the radical R preferably representing methyl is fixed in the 2'-, 4'- or 6'-position, an isomer mixture almost exclusively containing diisocyanates corresponding to formula (V), in which the radical R, preferably representing methyl, is situated only in the 2'- or 4'-position, also an isomer mixture corresponding to general formula (III), which almost exclusively contains diisocyanates corresponding to the following formula

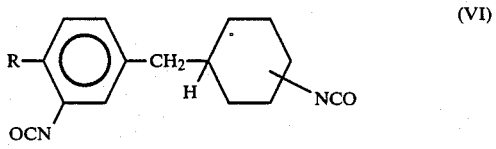

(VI)

in which about 80 to 95% of the aliphatically bound isocyanate groups are situated in the 2- or 4-position, and finally an isomer mixture corresponding to general formula (III), in which $R^1$ represents hydrogen and $R^2$ preferably represents methyl and in which more than 6090 of the isomers consist of diisocyanates corresponding to the following formula

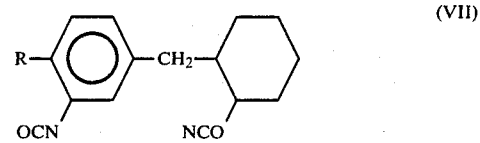

(VII)

in which R preferably represents methyl, may readily be produced by the processes mentioned above, optionally with inclusion of an isomer separation step. The above-mentioned isomer mixtures containing the diisocyanates of formulae (V) to (VII) as their main component are also preferred starting materials for the process according to the invention.

Pure isomers, for example the diisocyanate corresponding to formula (VIII) below

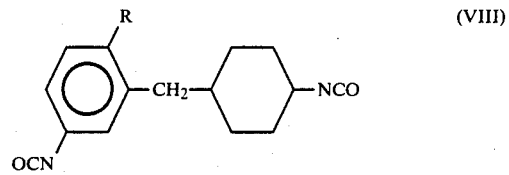

(VIII)

in which R is preferably methyl, and the diisocyanate corresponding to formula (IX)

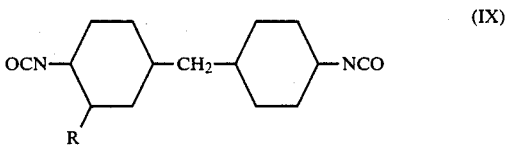

(IX)

in which R preferably represents methyl, are also obtainable by the above-mentioned processes and are suitable starting diisocyanates for use in the process according to the invention.

Other, equally readily obtainable and, hence, preferred starting materials for use in the production of the isocyanato-isocyanurates according to the invention are diisocyanates corresponding to formula (III), of the type obtainable by partial hydrogenation and subsequent phosgenation in accordance with DE-OS Nos. 3,245,320 and 3,245,321 from the mono- or di-alkyl-substituted diaminodiphenyl methanes accumulating in the mixed condensation of aniline and mono- and also dialkyl anilines with formaldehyde in accordance with DE-AS Nos. 2,133,870 and 2,149,998 and DE-OS No. 2,700,185, and also mixtures of those diisocyanates. In these diisocyanates or diisocyanate mixtures, the aromatically or aliphatically bound isocyanate groups are preferably situated in the 2'- or 4'- or in the 2- or 4-position to the methylene bridge. An isomer distribution such as this is shown, for example, by the isomer mixture corresponding to general formula (III) which predominantly contains diisocyanates corresponding to formula (X) below

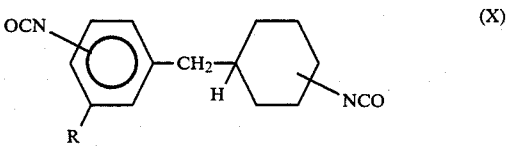

(X)

and which may be obtained as described from the mono-alkyl-substituted diaminodiphenyl methanes accumulating in the mixed condensation of ortho-alkyl anilines with aniline and formaldehyde. This isomer mixture preferably used as starting material contains more than about 90% by weight of diisocyanates corresponding to formula (X) and, in more than about 70% by weight of the material, the aliphatically and aromatically bound isocyanate groups are in the 4- or 4'-position to the methylene bridge.

Other starting materials readily obtainable by the method just described and preferably used for producing the isocyanato-isocyanurates according to the invention include an isomer mixture which exclusively contain diisocyanates corresponding to formula (XI) below

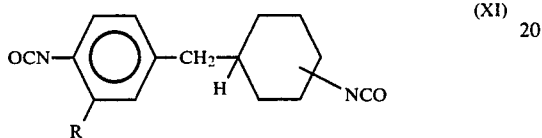

(XI)

and in which more than about 90% of the aliphatically bound isocyanate groups are in the 4-position, and pure isomers, for example the diisocyanate corresponding to formula (XII) below:

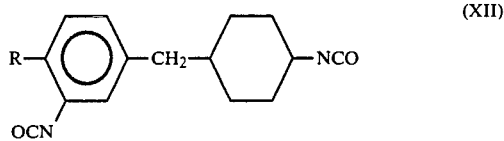

(XII)

In addition, (isocyanatobenzyl)-cyclohexyl isocyanates polyalkylated on the nucleus are also suitable starting materials for use in the process according to the invention.

Isomer mixtures which may be obtained particularly conveniently are, for example, the isomer mixtures corresponding to general formula (III) which may be obtained by the condensation of 2,6-dialkyl anilines with aniline and formaldehyde, followed by partial nucleus hydrogenation and phosgenation, and which consist predominantly (more than about 90% by weight) of diisocyanates corresponding to the following formula

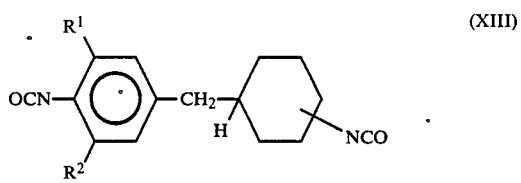

(XIII)

In these isomer mixtures, in which the substituents $R^1$ and $R^2$ preferably represent $C_1$–$C_3$ alkyl groups, from about 80 to 90% of the aliphatically bound isocyanate groups are situated in the 2- or 4-position.

Pure isomers, for example the diisocyanates (XIV), (XV) and (XVI), are also obtainable in this way, optionally with inclusion of an isomer separation step, and may be successfully used for producing the isocyanato-isocyanurates according to the invention.

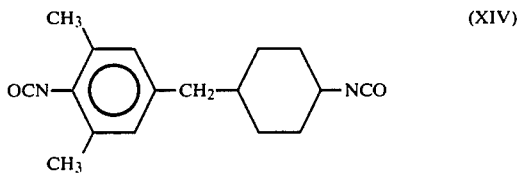

(XIV)

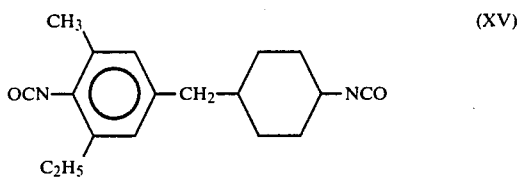

(XV)

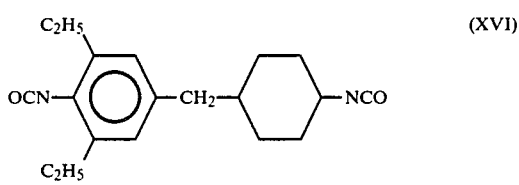

(XVI)

Finally, another suitable starting material is 1-(4'-isocyanatobenzyl)-4-isocyanatocyclohexane which may be obtained by phosgenation from the 1-(4'-amino-benzyl)-4-aminocyclohexane obtainable in accordance with U.S. Pat. No. 2,511,028.

The manner in which the process according to the invention is carried out depends to a large extent on whether the isocyanato-isocyanurates according to the invention are to be obtained in substantially monomer-free form in a single step or whether the trimerization products are to be freed from monomers in a second step, for example by subsequent thin-layer distillation. In the first case, the trimerization reaction is terminated at a degree of trimerization of from about 50 to 75% and preferably from about 50 to 60% (the "degree of trimerization" is to be understood to be the percentage of isocyanate groups present in the starting diisocyanate which react to form trimers). Since the isocyanato-isocyanurates accumulating have a resin-like, solid consistency and normally can no longer be stirred at temperatures below about 100° C., it is necessary to carry out this variant of the process according to the invention in the presence of solvents of the type mentioned by way of example in the following. Where unreacted starting diisocyanate is removed on completion of the trimerization reaction, the trimerization reaction is generally terminated at a degree of trimerization of from about 10 to 60% and preferably from about 10 to 40%, followed by the known removal of unreacted starting diisocyanate, for example by thin-layer distillation. This variant of the process according to the invention is preferably carried out in solvent-free form.

In principle, any compounds which accelerate the trimerization of isocyanate groups may be used as catalysts in the process according to the invention. Suitable catalysts are, for example, (a) strong organic bases,
(b) tertiary amines of high basicity,
(c) tertiary amines in conjunction with other bases,
(d) Friedel-Crafts catalysts,
(e) carboxylic acid salts,
(f) alkali metal oxides, alcoholates, phenolates, hydroxides, carbonates, (g) onium compounds based on nitrogen, phosphorus, arsenic, antimony, sulfur, selenium, (h) phosphines and phosphites, (i) metal salts in conjunction with phase-transfer catalysts and (k) transition metal compounds.

Other catalysts which do not belong to the classes of compounds mentioned above may of course also be used.

However, in selecting the particular catalyst, it is important to take into account which of the above-mentioned processes is to be used for producing the isocyanato-isocyanurates according to the invention.

If the products are to be directly obtained in substantially monomer-free form, it is advisable to use catalysts with which it is possible to obtain largely selective trimerization of the aromatically bound isocyanate group.

Of these catalysts, Mannich bases obtainable from phenols, secondary amines and aldehydes or ketones, in admixture with tertiary amines of high basicity have proved to be particularly suitable. One particularly suitable catalyst system of this type is, for example, a mixture of 2-(N,N-dimethylaminomethyl)-4-nonylphenol and 1,4-diazabicyclo-(2,2,2)-octane. When this catalyst system is used, the Mannich base is generally used in a quantity of from about 0.01 to 3% by weight and preferably in a quantity of from about 0.1 to 1.0% by weight, while the tertiary amine is generally used in a quantity of from about 0.01 to 5% by weight and preferably in a quantity of from about 0.02 to 1.0% by weight, based in each case on the weight of the diisocyanate used.

Other tertiary amines or amine mixtures having sufficiently high catalytic activity may also be used as catalysts for selective trimerization of the aromatically bound isocyanate group. In this case, too, quantities of from about 0.01 to 5% by weight, based on the weight of the diisocyanate used, are generally sufficient.

When the products according to the invention are produced in two stages, it is of advantage to use the selective catalysts mentioned when isocyanato-isocyanurates predominantly or exclusively containing aliphatically bound isocyanate groups are to be obtained.

When the catalysts mentioned by way of example which selectively accelerate trimerization of the aromatic isocyanate groups are used, it is possible both in the single-stage process and also in the two-stage process to obtain isocyanato-isocyanurates wherein about 90 to 100% of the isocyanate groups are cycloaliphatically bound isocyanate groups.

For producing mixed isocyanato-isocyanurates, i.e. isocyanato-isocyanurates containing both aromatically and also cycloaliphatically bound isocyanate groups, it is advisable to use stronger, less selective catalysts. Suitable catalysts of this type are, for example, strong organic bases such as alkali or alkaline-earth alcoholates and phenolates, the alkali salts of lower carboxylic acids, particularly potassium acetate, preferably complexed in accordance with DE-OS No. 3,100,262 or DE-OS No. 3,100,263, and also quaternary ammonium hydroxides. Within the class of compounds just mentioned, tetraalkyl ammonium hydroxides containing hydroxyl groups, for example N,N,N-trimethyl-N-(2-hydroxypropyl)-ammonium hydroxide, have proven to be particularly suitable. When the non-selective catalysts are used, the quantity of catalyst used generally amounts to between about 0.01 and 3% by weight and preferably to between about 0.1 and 1.0% by weight, based in each case on the weight of the isocyanate used. The other catalysts may also be used in quantities of this order.

The catalyst or catalyst mixture may be added to the reaction mixture either in solid or liquid solvent-free form or in dissolved form, depending on the production process. Depending on the particular catalyst used, suitable solvents are, for example, toluene, xylene, ethyl acetate, ethyl glycol acetate, N,N-dimethyl formamide. Compounds containing hydroxy groups such as methanol, 2-ethyl hexanol, diethylene glycol and similar compounds, may also be used, provided they are employed in small quantities and their use does not adversely affect the resulting products.

The production of the isocyanato-isocyanurates according to the invention is generally carried out at a temperature in the range from about 20 to 120° C., depending on the type of catalyst used. When the catalyst system containing 2-(N,N-dimethylaminomethyl)-4-nonylphenol and 1,4-diazabicyclo-(2,2,2)-octane is used, the preferred temperature is in the range from about 30° to 80° C. and, more particularly, in the range from about 40° to 60° C. When the catalyst preferred for less selective trimerization is used, namely N,N,N-trimethyl-N-(2-hydroxypropyl)-ammonium hydroxide, similar temperature ranges are preferred.

The trimerization reaction which takes place in the process according to the invention is generally terminated at the particular degree of trimerization required by thermal decomposition of the catalyst and/or by the addition of a catalyst poison. It is only when selective catalysts of the type mentioned by way of example are used in the one-stage process that such a measure may be dispensed with because the reaction can often be slowed down to a considerable extent at the reaction temperature selected after trimerization of the aromatic isocyanate groups (degree of trimerization=50%) and virtually terminated simply by cooling to room temperature. However, it is advisable in this case, too, always to destroy the catalyst used to increase the shelf life of the products. When the two-stage process in which the starting materials are only partly reacted (degree of trimerization 10 to 60%) is used, reliable termination of the reaction is essential.

Thermal termination (where thermally decomposable catalysts are used) may be carried out either by briefly heating the reaction mixture to 80°-150° C. or by using catalysts which are thermally labile at the reaction temperature selected, so that the catalysts used "exhaust themselves." In this case, the required degree of trimerization may be determined in advance simply by appropriately selecting the quantity of catalyst used. The second method of terminating the reaction is to use catalyst poisons which, in most cases, are highly acidic or alkylating compounds. Suitable catalyst poisons are, for example, 2-ethyl hexanoic acid, perfluorobutane sulfonic acid, toluene sulfonic acid methyl ester or toluene sulfonic acid ethyl ester. In many cases, compounds which readily split off chloride such as benzoyl chloride, phosphorus trichloride, phosphorus oxychloride or trimethyl chlorosilane, may also be successfully used for termination.

The minimum time required to obtain complete thermal or chemical deactivation of the catalyst depends to a large extent upon the type and quantity of catalyst and co-catalyst, if any, used and also upon the type of catalyst poison used. As already mentioned, the temperature at which trimerization is carried out can also have a considerable bearing on the time required for terminating the reaction. The optimal conditions for termination, like the other reaction parameters, may readily be determined in preliminary tests.

When the process according to the invention is carried out on the basis of the embodiment in which the starting diisocyanate to be trimerized is reacted in a single stage up to a degree of trimerization of at least about 50%, the reaction is carried out in the presence of solvents as already mentioned. The quantity of solvent used generally amounts to between about 5 and 80% by weight and preferably to between about 20 and 50% by weight, based on the reaction mixture as a whole. Suitable solvents are, in particular, solvents which are suitable for the further processing of the isocyanato-isocyanurates, i.e. the solvents inert to isocyanate groups which are normally used in the lacquer industry such as toluene, xylene, di-(2-butyl)-ether, methyl acetate, ethyl acetate, butyl acetate, methyl isobutyl ketone, diethylene glycol dimethyl ether, 2-ethoxy ethyl acetate, 2-methoxy propyl acetate, 2-methoxy ethyl acetate, 2-nitropropane or dimethyl acetamide. It is also possible to use mixtures of different solvents or mixtures of true solvents and diluents which do not have a dissolving effect, such as for example hexane, isooctane or decalin.

This embodiment of the process according to the invention may be carried out, for example as follows:

The diisocyanate or diisocyanate mixture used as a starting material is introduced into the reaction vessel under nitrogen in the form of an about 20 to 95%, preferably about 50 to 80% solution in 2-ethoxyethyl acetate or any other suitable solvent and heated to a temperature in the range from about 20° to 80° C., for example to about 40° C. The catalyst or catalyst mixture is then introduced.

Where the catalyst system containing 2-(N,N-dimethylaminomethyl)-4-nonyl phenol and 1,4-diaza-bicyclo-(2,2,2)-octane is used, the trimerization of the araliphatic diisocyanates corresponding to formula III takes place slowly and steadily without any incubation period. If trimerization does not progress sufficiently quickly or sufficiently far, the reaction may be recatalyzed as often as required until the desired conversion is reached. The catalyst may also be continuously added to the reaction mixture over the entire duration of the trimerization reaction.

The reaction mixture is then stirred at the reaction temperature until the required degree of trimerization is reached. This degree of trimerization may be determined simply by measuring the NCO-content of the reaction mixture. In this way, it is possible to obtain solutions of isocyanato-isocyanurates which have a residual monomer content (content of unreacted starting diisocyanate) of less than about 2% by weight and preferably less than about 0.5% by weight, based on solution. It is also possible with a view to monitoring the reaction to continuously check this residual monomer content and to terminate the reaction at the desired residual monomer content. To this end, the residual monomer content may be rapidly determined, for example, by gas, liquid or thin-layer chromatography of the optionally derivatized samples taken. When the calculated NCO-content or the desired monomer content is reached, the catalyst is deactivated as described above, i.e. either thermally by brief heating to about 120° C. for example or chemically by the addition of a catalyst poison such as toluene sulfonic acid methyl ester.

However, this method of producing the isocyanato-isocyanurates according to the invention in a single step only leads to substantially monomer-free products in a smooth reaction when the diisocyanates used do not show any serious steric hindrances of the aromatically bound isocyanate groups, which is often the case when both ortho positions to the aromatically bound isocyanate group are substituted by alkyl groups.

Both in the production of isocyanato-isocyanurates containing aliphatically and aromatically bound isocyanate groups using non-selective catalysts or using starting diisocyanates containing sterically hindered aromatic isocyanate groups and also in the production of isocyanato-isocyanurates having a high content of mono-isocyanurates corresponding to general formula (I) (p=1), it is advisable to carry out the process according to the invention on the basis of the second embodiment which is carried out in the absence of solvents, and in which the trimerization reaction is terminated at a lower trimerization degree as mentioned above. After the trimerization reaction, the excess starting diisocyanate is then generally removed from the reaction mixture by thin-layer distillation or otherwise until isocyanato-isocyanurates having a residual monomer content of less than about 2% by weight and preferably less than about 0.5% by weight remain. In this case, too, the content of cycloaliphatically bound isocyanate groups in the end products may be influenced through the choice of the catalyst and starting diisocyanate used.

The second embodiment of the process according to the invention may be carried out, for example, as follows:

The starting diisocyanate is introduced into the reaction vessel, preferably in the absence of air, and heated to a temperature in the range from about 20° to 80° C., for example about 60° C. The catalyst, optionally in solution, is then introduced. The trimerization reaction normally begins while the catalyst is being introduced into the isocyanate as reflected in a gradual increase in temperature to around 70°–80° C.

The reaction mixture is then stirred at this temperature or, if desired, at another temperature until the required degree of trimerization is reached. Where thermally labile catalysts which gradually decompose under the reaction conditions are used, more catalyst may optionally be added either in portions or continuously during the reaction. After termination of the trimerization reaction by thermal decomposition of the catalyst or by the addition of a catalyst poison, the starting diisocyanate still present in the reaction mixture is generally removed by distillation using a thin-layer evaporator having wall temperatures of from about 180° to 250° C. and a pressure of from about 0.1 to 2 mbar and preferably from about 0.5 to 1 bar to obtain products having a monomer content of less than about 2% by weight and preferably of less than about 0.5% by weight. The sump products accumulating are generally highly viscous or solid resins which become thinly liquid at about 80° to 180° C., depending on the type of starting diisocyanate used and upon the production conditions.

In general, they may readily be dissolved in the usual lacquer solvents to give substantially colorless to pale yellow solutions which generally have viscosities of from about 600 to 3000 mPas (25° C.) at a solids content of 60%. As can be shown by gel chromatography, the molecular weight distribution of the products obtained by the process according to the invention depends to a large extent upon the constitution of the diisocyanates used (free or sterically hindered aromatic isocyanate group) and upon the type of catalyst used (selective or non-selective catalysts). When diisocyanates showing a distinct steric hindrance of the aromatic isocyanate group are used in combination with non-selective catalysts, it is possible that, at a degree of trimerization of only 30%, the content of pure trimers corresponding to general formula (I) (p=1) amounts to only about 30 to 50% by weight, based on all the isocyanato-isocyanurates. On the other hand, when sterically unhindered diisocyanates and selective catalysts are used, it is possible to obtain isocyanato-isocyanurates containing up to about 90% of pure trimers for a degree of trimerization of, for example, 50%. Isocyanato-isocyanurates according to the invention containing more than about 90% of pure trimers can be obtained, for example, using sterically unhindered diisocyanates and selective catalysts for degrees of trimerization kept below 50%. In addition to the pure trimers, the isocyanato-isocyanurates according to the invention contain linear, higher homologs corresponding to general formula (I) (p=2-5) and non-linear, higher homologs of the type previously mentioned. The non-linear higher homologs may be present in a proportion of up to 50% by weight, based on all the isocyanato-isocyanurates. However, they are generally present in a proportion of from 0 to about 10% by weight. Accordingly, at least about 90% by weight of the preferred isocyanato-isocyanurates according to the invention are compounds corresponding to general formula (I).

Products obtained by the process according to the invention, of which the isocyanate groups are for the most part aromatically bound, are formed when diisocyanates are used in which the aliphatically bound isocyanate groups are not hindered, while their aromatically bound isocyanate groups are very strongly hindered, for example by two isopropyl groups in the ortho position.

Accordingly, by varying the above-mentioned parameters it is possible to influence the composition of the products obtained by the process according to the invention as required. Accordingly, it is possible by the process according to the invention to produce isocyanato-isocyanurates having a high or low content of aliphatically bound isocyanate groups and a high or low content of pure trimers.

The isocyanato-isocyanurates according to the invention are generally distinguished, largely irrespective of their constitution, by good to very good compatibility with apolar solvents. The isocyanato-isocyanurates obtainable from asymmetrical diisocyanates having relatively long alkyl side chains show particularly good miscibility with apolar solvents such as toluene or xylene. It is only the isocyanato-isocyanurates based on non-alkyl-substituted diisocyanates which show lessened compatibility with apolar solvents, particularly when they consist very largely of pure trimers.

The isocyanato-isocyanurates according to the invention containing exclusively or almost exclusively aliphatically bound isocyanate groups are distinguished by comparatively low reactivity to compounds containing hydroxy groups and other compounds reacting with isocyanate groups. For this reason, the isocyanato-isocyanurates according to the invention are interesting polyisocyanates for polyurethane lacquers which are required to have a long pot life or in whose case hardening of the coating can only be obtained by heat treatment. These relatively sluggishly reacting compounds according to the invention are also eminently suitable for use as the polyisocyanate component in powder lacquers in which it is important to be able to mix the polyol component and the polyisocyanate component homogeneously with one another without the two components entering into a significant reaction.

The isocyanato-isocyanurates according to the invention which, in addition to aliphatically bound isocyanate groups also contain a considerable number of aromatically bound isocyanate groups may be used with considerable effect in lacquer systems of the type in which the isocyanate component is required to show graduated reactivity. They may also be used in systems where rapid initial drying is required.

Irrespective of the process used for their production, the isocyanato-isocyanurates according to the invention have very little color of their own so that they are eminently suitable for the production of light-stable, colorless surface lacquers.

This applies in particular to the isocyanato-isocyanurates exclusively containing aliphatically bound isocyanate groups and hence to the coatings produced therefrom which show extremely high light stability of a degree which would otherwise be achieved only by products based on purely aliphatic isocyanates.

Reactants for the isocyanato-isocyanurates according to the invention when they are used in accordance with the invention, i.e. to produce isocyanate polyaddition products, preferably polyurethane lacquers, are the compounds containing isocyanate-reactive groups normally used to produce these products and in particular the polyhydroxyl compounds having a molecular weight in the range from about 62 to 10,000 which are known from the chemistry of polyurethane lacquers, preferably polyhydroxy polyesters having a molecular weight in the range from about 800 to 4000 and/or polyhydroxy polyacrylates having a molecular weight in the same range. For their use in accordance with the invention, the isocyanato-isocyanurates according to the invention are generally employed in a quantity which corresponds to an equivalent ratio of isocyanate groups to isocyanate-reactive groups of from about 0.8:1 to 3:1 and preferably from about 0.9:1 to 1.1:1.

For their use in accordance with the invention, the isocyanato-isocyanurates according to the invention may also be used in a form in which they are blocked by blocking agents for isocyanate groups. Suitable blocking agents are the compounds known per se from the chemistry of polyurethane lacquers such as phenol, cresols, acetoactic acid ethyl ester, acetyl actone, malonic acid diethyl ester, butanone oxime or ε-caprolactam. The blocking of the isocyanato-isocyanurates according to the invention may be carried out either in the absence of solvents or in solution. Thus, it is possible for example to react solutions of the isocyanato-isocyanurates according to the invention in the particular solvent used for their preparation with the blocking agent.

Any auxiliaries and additives known from lacquer technology such as solvents, pigments, fillers, catalysts, levelling aids and the like, may of course also be used in the polyurethane lacquers in which the isocyanato-isocyanurates according to the invention are present, optionally in blocked form, as the polyisocyanate component.

The diisocyanates A-K described hereinafter were used as starting materials in the following Examples. The data provided in regard to composition were determined by gas chromatography. All the percentages quoted are percentages by weight.

Diisocyanate A

As described in U.S. Pat. No. 3,663,514 4,4'-diaminodiphenyl methane was partially hydrogenated to form 4-(4'-aminobenzyl)-cyclohexylamine, followed by reaction with phosgene to form 4-(4'-isocyanatobenzyl)-cyclohexyl isocyanate. The NCO-content of the distilled product amounted to 32.7%.

Composition:
>98% of 4-(4'-isocyanatobenzyl)-cyclohexyl isocyanate (cis- and trans-isomer)
<1% of 4,4'-diisocyanatodiphenyl methane
<1% of 4,4'-diisocyanatodicyclohexyl methane.

Diisocyanate B 2500 g (11.8 moles) of the diamine mixture distilling at 150°-200° C. (0.133 mbar), which is described in Example 8(c) of EP-A 024,665, and 50 g of a commercially available ruthenium-aluminum oxide supported catalyst (5% of Ru) were introduced into a 5 liter capacity stirrer-equipped autoclave, followed by the addition of 100 g of ammonia after repeated purging with nitrogen and hydrogen.

The reaction mixture was then heated to 135°-145° C. and stirred under a hydrogen pressure of 180 to 200 bars until 36 moles of hydrogen had been taken up. After cooling to room temperature, the reaction mixture was expanded to normal pressure, dissolved in methanol and the catalyst separated off by filtration during two washes with methanol. All product-containing solutions were combined and subjected to distillation. 1905 g of a product boiling at 165° to 177° C. (2.5 to 3.5 mbars) were obtained, containing 94.7%—according to analysis by gas chromatography —of isomeric (aminomethylbenzyl) cyclohexylamines, 0.4% of isomeric, perhydrogenated diamines and 5.9% of unreacted starting material.

1000 g of this product were then dissolved in 10 liters of chlorobenzene and the resulting solution stirred slowly into a solution kept at 5° C. of 2000 g of phosgene in 20 liters of chlorobenzene, the temperature of that solution rising to 20° C. After stirring for 2 hours at 20° C., the suspension formed was heated to 60° C. and then stirred until all the solids had dissolved.

The reaction mixture was then heated to 120° C. over a period of 2 hours, during which phosgene was introduced, and then stirred at that temperature for another 2 hours, during which more phosgene was introduced. Excess phosgene was removed by refluxing and, at the same time, passing nitrogen through while the solvent was removed in a thin-layer evaporator, leaving 1347 g of crude isocyanate having an NCO-content of 27.8%.

After redistillation, 908 g of a product now having an NCO-content of 30.3% were obtained. The boiling point at 0.7 mbar was 168° C. and the viscosity at 25° C. was 18 mPas.

Composition:
98% of (isocyanato-methylbenzyl)-cyclohexyl isocyanates, including
15 to 20% of 2-(3'-isocyanato-2'(4',6')-methylbenzyl)-cyclohexyl isocyanates,
55 to 60% of 4-(3'-isocyanato-2'(4',6')-methylbenzyl)-cyclohexyl isocyanates and approximately 30% of other isomers:
approximately 0.5% of unidentified diisocyanatomethyl dicyclohexyl methanes,
approximately 1.5% of unidentified diisocyanatomethyl diphenyl methanes.

Diisocyanate C 500 g (2.36 moles) of a diamine mixture, containing 78% of 4,4'-diamino-3-methyl diphenyl methane, 16% of 4,2'-diamino-3-methyl diphenyl methane and 6% of unidentified diaminodiphenyl methanes, were hydrogenated in the presence of 50 g of a commercially available ruthenium catalyst (5% of ruthenium on aluminum oxide) and 50 g of ammonia using the method described for diisocyanate B.

On completion of the reaction, the crude product was taken up in methanol, the catalyst was filtered off and washed and the combined solutions were subjected to fractional distillation under reduced pressure. 357 g of diamine boiling at 125°-135° C. (0.1 mbar) and containing 98% 4-(4'-amino-3'-methylbenzyl)-cyclohexylamine or 2-(4'-amino-3'-methylbenzyl)-cyclohexylamine and 2% of isomeric diaminomethyl dicyclohexyl methanes, were obtained in the main fraction.

This product was then dissolved in 2.6 liters of chlorobenzene and the resulting solution slowly added dropwise to a solution, cooled to −5° C. to −8° C., of 800 g of phosgene in 2.6 liters of chlorobenzene. The suspension formed was then stirred for 2 hours at room temperature and subsequently heated to 130° C. while phosgene was introduced (at a rate of 150 g/h). The mixture was then stirred at 130° C. for another 2 hours, during which more phosgene was introduced.

Working up of the reaction mixture by distillation gave as the main fraction 402 g of a colorless liquid of which the boiling point at 0.05 mbar was 130°-135° C. and its NCO-content was 30.8%. The viscosity measured at 25° C. amounted to 50 mPas.

Composition:
82% of 4-(4'-isocyanato-3'-methylbenzyl)-cyclohexyl isocyanate
17% of 2-(4'-isocyanato-3'-methylbenzyl)-cyclohexyl isocyanate
approximately 1% of unidentified diisocyanatomethyl diphenyl methanes.

Diisocyanate D

Following the procedure described for diisocyanate B, 500 g (2.21 moles) of a diamine mixture of the following composition produced in accordance with EP-A 46,556 (Example 5):

1.9% of a mixture of 2,2'-diamino-4- and 2,2'-diamino6-ethyl diphenyl methane, 11.1% of 4,2'-diamino-2-ethyl diphenyl methane, 20.1% of a mixture of 3,2'-diamono-2-, 3,2'-diamino-4- and 3,2'-diamino-6-ethyl diphenyl methane 66.1% of a mixture containing more than 80% of 3,4'-diamino-2-, 3,4'-diamino-4- and 3,4'-diamino-6-ethyl diphenyl methane and which contained up to 20% of other diaminoethyl diphenyl methanes, and 0.8% of unknown triamines, were hydrogenated with 6.6 moles of hydrogen in the presence of 50 g of ruthenium-aluminum oxide supported catalyst (5% of ruthenium on aluminum oxide) and 50 g of ammonia in a 1.5 liter stirrer-equipped autoclave.

On completion of the reaction, the crude product obtained was taken up in methanol, the catalyst was filtered off and washed and the combined methanolic solutions were subjected to fractional distillation under reduced pressure. 360 g of a diamine mixture boiling at 125°-136° C. (0.05 mbar), containing 93.5% of various (aminoethylbenzyl)-cyclohexylamines having an isomer composition corresponding to the starting product, 2.9% of isomeric diaminoethyl dicyclohexyl methanes and 3.5% of unhydrogenated starting material, were obtained as the main fraction. This product was dissolved in 2.4 liters of chlorobenzene and the resulting solution slowly added to a solution, cooled to −5° to −10° C., of 540 g of phosgene in 2.4 liters of chlorobenzene. The suspension obtained was then heated to 130° C. while phosgene was introduced (100 g/h), followed by stirring at 130° C. for another 2 hours during which more phosgene was introduced. Working up of the reaction mixture by distillation produced as the main fraction 374 g of a liquid boiling at 140°–144° C. (0.1 mbar), of which the NCO content amounted to 29.6% and its viscosity at 25° C. amounted to approximately 50 mPas.

Composition:
>99% of isomeric (isocyanatoethylbenzyl)-cyclohexyl isocyanates with an isomer composition corresponding to the starting product.

Diisocyanate E 1440 g (6.37 moles) of a diamine mixture containing 65% of 3,4′-diamino-4-ethyl diphenyl methane 32% of 3,4′-diamino-2-ethyl diphenyl methane and 3% of other, unidentified diaminoethyl diphenyl methanes, were mixed with 900 ml of tert.-butanol and the resulting mixture reacted with 20 moles of hydrogen in the presence of 140 g of ruthenium-aluminum oxide supported catalyst (5% of ruthenium) in a 3 liter stirrer-equipped autoclave. The temperature prevailing during the hydrogenation reaction was 130° C. and the hydrogen pressure was 150–250 bars.

On completion of the reaction, the crude product obtained was taken up in methanol, the catalyst was filtered off and washed and the methanolic solutions were subjected to fractional distillation under reduced pressure. 810 g of a diamine mixture boiling at 135°–140° C. (0.1 mbar) and containing 99% of isomeric 4-(3′-amino-4′(2′)-ethylbenzyl)-cyclohexyl amines, were obtained as the main fraction.

580 g of this product were dissolved in 3.1 liters of chlorobenzene and the resulting solution slowly added to a solution, cooled to −5° to −10° C., of 1000 g of phosgene in 3.1 liters of chlorobenzene. The finely divided suspension obtained was subsequently stirred without cooling for 1.5 hours, heated to 130° C. while more phosgene (100 g/h) was introduced and then stirred at that temperature for another 4 hours during which more phosgene was introduced.

Working up of the reaction mixture by distillation produced as the main product 630 g of a colorless liquid boiling at 150°–155° C. (0.1 mbar) which had an NCO content of 29.6% and a viscosity at 25° C. of approximately 50 mPas.

Composition:
65% of 4-(4′-ethyl-3′-isocyanatobenzyl)-cyclohexyl isocyanate
34% of 4-(2′-ethyl-3′-isocyanatobenzyl)-cyclohexyl isocyanate
approximately 1% of other, unidentified diisocyanates.

Diisocyanate F

Following the procedure described for diisocyanate B, 452 g (2 moles) of 4,2′-diamino-3,5-dimethyl diphenyl methane were reacted with 6.0 moles of hydrogen in the presence of 45 g of ruthenium-aluminum oxide supported catalyst (5% of ruthenium) and 45 g of ammonia in a 1.5 liter stirrer-equipped autoclave.

On completion of the reaction, the crude product obtained was taken up in methanol, the catalyst was filtered off and washed and the combined methanolic solutions were subjected to fractional distillation under reduced pressure. 457 g of a diamine mixture boiling at 114°–152° C. (0.015 mbar), containing 93% of 2-(4′-amino-3′,5′-dimethylbenzyl)-cyclohexylamine, 6.3% of 4,2′-diamino-3,5-dimethyl dicyclohexyl methane and 0.6% of unreacted starting material, were obtained as the main fraction.

This product was dissolved in 2 liters of chlorobenzene and the resulting solution was slowly added to a solution, cooled to −5° to −10° C., of 800 g of phosgene in 1.7 liters of chlorobenzene. The suspension obtained was then heated to 120° C. while phosgene was introduced (120 g/h) and stirred under the same conditions for another 3 hours. Working up by distillation produced as the main product 502 g of a colorless liquid boiling at 126° C. (0.06 mbar), of which the NCO-content amounted to 29.6% and its viscosity at 25° C. amounted to approximately 100 mPas.

Composition:
99.5% of 2-(4′-isocyanato-3′,5′-dimethyl)-cyclohexyl isocyanate.
0.5% of other unidentified compounds.

Diisocyanate G

Following the procedure described for diisocyanate B, 500 g (1.96 moles) of an amine mixture containing 80% of 4,4′-diamino-3,5-diethyl diphenyl methane, 13% of 4,2′-diamino-3,5-diethyldiphenyl methane, 3% of 4,4′- and 2,4′-diaminodiphenyl methane and 2.5% of 4,4′-diamino-3,3′,5,5′-tetraethyl diphenyl methane, were reacted with 6 moles of hydrogen in the presence of 50 g of ruthenium-aluminum oxide supported catalyst (5% of ruthenium and 50 g of ammonia.

On completion of the reaction, the crude product obtained was taken up in methanol, the catalyst was filtered off and washed and the combined methanolic solutions were subjected to fractional distillation under reduced pressure. 340 g of a diamine mixture boiling at 136°–140° C. (0.1 mbar) containing 94% of isomeric (4′-amino-3′,5′-diethylbenzyl)-cyclohexylamines, 1.8% of isomeric diaminodiethyl dicyclohexyl methanes, 1.2% of unreacted starting amines and 3% of other, unidentified diamines, were obtained as the main fraction.

This product was dissolved in 1.8 liters of chlorobenzene and the resulting solution slowly added to a solution, cooled to −5° to −10° C., of 530 g of phosgene in 1.8 liters of chlorobenzene. The suspension obtained was then heated to approximately 130° C. while phosgene was introduced (120 g/h), followed by refluxing for another 3 hours during which more phosgene was introduced.

Working up of the reaction mixture by distillation produced as the main product 350 g of a colorless liquid boiling at around 135° C. (0.05 mbar), of which the NCO-content amounted to 27% and its viscosity at 25° C. amounted to 90 mPas.

Composition:
84% of 4-(4′-isocyanato-3′,5′-diethylbenzyl)-cyclohexyl isocyanate
14% of 2-(4′-isocyanato-3′,5′-diethylbenzyl)-cyclohexyl isocyanate
approximately 1% of unidentified diisocyanatodiethyl dicyclohexyl methanes
approximately 1% of other, unidentified diisocyanates.

Diisocyanate H

Following the hydrogenation procedure described for diisocyanate B, 500 g (1.78 moles) of a diamine mixture containing 80% of 4,4'-diamino-3,5-diisopropyl diphenyl methane, 12% of 4,2'-diamino-3,5-diisopropyl diphenyl methane and 6% of other, unidentified diaminodipropyl diphenyl methanes, were reacted with 8.1 moles of hydrogen in the presence of 50 g of ruthenium-aluminum supported catalyst (5% of ruthenium) and 50 g of ammonia.

On completion of the reaction, the crude product obtained was taken up in methanol, the catalyst was filtered off and washed and the combined methanolic solutions were subjected to fractional distillation under reduced pressure. 428 g of a diamine mixture containing 99% of isomeric (4'-amino-3',5'-dipropylbenzyl)-cyclohexylamines, 0.5% of isomeric diaminodipropyl dicyclohexyl methanes and 0.5% of starting material, were obtained as the main product.

This product was dissolved in 2 liters of chlorobenzene and the resulting solution slowly added to a solution, cooled to -5° to -10° C., of 600 g of phosgene in 2 liters of chlorobenzene. The suspension obtained was subsequently heated to approximately 130° C. while phosgene was introduced (120 g/h), followed by refluxing for another 2 hours during which more phosgene was introduced. Working up of the reaction mixture by distillation produced as the main product 458 g of a liquid boiling at 170° to 190° C. (0.1 mbar) which had an NCO-content of 24.6% and a viscosity at 25° C. of approximately 500 mPas.

Composition:
- 83% of 4-(4'-amino-3',5'-diisopropyl-benzyl)-cyclohexyl isocyanate
- 12% of 2-(4'-amino-3',5'-diisopropyl-benzyl)-cyclohexyl isocyanate
- 5% of 2(4)-(4'-amino-3'-isopropyl-5'-n-propyl-benzyl)-cyclohexyl isocyanate Diisocyanate K Following the hydrogenation procedure described for diisocyanate B, 500 g (2.1 moles) of a diamine mixture containing 82% of 4,4'-diamino-3-ethyl-5-methyl diphenyl methane, 13% of 4,2'-diamino-3-ethyl-5-methyl diphenyl methane, 2.5% of 4(2), 4'-diaminodiphenyl methane and 2.5% of 4(2), 4'-diamino-3,3'-diethyl-5,5'-dimethyl diphenyl methane, were reacted with 6.3 moles of hydrogen in the presence of 50 g of ruthenium-aluminum oxide supported catalyst (5% of ruthenium) and 50 g of ammonia.

On completion of the reaction, the crude product obtained was taken up in methanol, the catalyst was filtered off and washed and the combined methanolic solutions were subjected to fractional distillation under reduced pressure 440 g of a diamine mixture boiling at 120°-125° C. (0.05 mbar) and containing 97% of isomeric 4(2)-(4'-amino-3'-ethyl-5'-methylbenzyl)-cyclohexyl amines and 3% of other, unidentified diamines, were obtained as the main product.

This product was dissolved in 2.5 liters of chlorobenzene and slowly added to a solution, cooled to −5° to −10° C., of 900 g of phosgene in 2.5 liters of chlorobenzene. The suspension obtained was heated to 130° C. while phosgene was introduced (100 g/h), followed by refluxing for another 2 hours during which more phosgene was introduced. Working up of the reaction mixture by distillation produced as the main product 497 g of a liquid boiling at 133° to 135° C. (0.05 mbar) which had an NCO-content of 28.2% and a viscosity at 25° C. of approximately 100 mPas.

Composition:
- 85% of 4-(4'-isocyanato-3'-ethyl-5'-methylbenzyl)-cyclohexyl isocyanate
- 14% of 2-(4'-isocyanato-3'-ethyl-5'-methylbenzyl)-cyclohexyl isocyanate
- 1% of other, unidentified diisocyanates.

EXAMPLE 1

100 g (0.39 mole) of diisocyanate A were mixed under nitrogen with 40 g of ethyl glycol acetate, followed by the addition with stirring of 26.7 g of a 10% solution of 2-(N,N-dimethylaminomethyl)-4-nonylphenol in ethyl glycol acetate.

A distinctly exothermic reaction began spontaneously, as a result of which the temperature rose to 40° C. in 10 minutes. During the further course of the reaction, the temperature was kept constant at 40°-45° C. by gentle cooling—and gentle heating towards the end of the reaction.

After 6 hours, the NCO-content had fallen to 9.5%. 1.8 g of toluene sulfonic acid methyl ester were added and the reaction mixture was stirred for 1 hour at 100° C. (degree of trimerization: 52%).

On cooling to room temperature, the hitherto clear solution became distinctly cloudy. After standing for another 2 days, the product had assumed a paste-like character. The monomer content as determined by gel chromatography amounted to approximately 0.8%, based on the mixture as a whole. The pure trimer content of the solid amounted to 84% (uncorrected value), while the content of relatively high molecular weight fractions containing more than 3 isocyanurate units amounted to approximately 5%. After hydrolysis of the isocyanate groups, the content of aromatically and aliphatically bound amine groups was determined by titrimetry and less than 2% of all the amine functions were aromatic in character.

EXAMPLE 2

1800 g (6.7 moles) of diisocyanate B were mixed with 960 g of ethyl glycol acetate, followed—after dry nitrogen had been passed over—by the addition with stirring of 23 g of 2-(N,N-dimethylaminomethyl)-4-nonylphenol and 0.45 g of 1,4-diazabicyclo-(2,2,2)-octane in 105 g of ethyl glycol acetate.

The reaction which began spontaneously produced an increase in temperature from 20° C. to 40°-45° C. over a period of 30 minutes. During the further course of the reaction, the temperature was kept constant at approximately 40° C., initially by occasional cooling and later by gentle heating. After 8 hours, the NCO-content had fallen to 8.1%. 112 g of a 20% solution of toluene sulfonic acid methyl ester in ether glycol acetate were then added and the reaction mixture was subsequently stirred for 1 hour at 100° C. It was then left to cool to room temperature (degree of trimerization: 57%).

The product obtained was substantially colorless and had an NCO-content of 7.8%. Its viscosity amounted to 2200 mPas at 25° C. and its monomer content, according to analysis by gel chromatography, to less than 0.5%, based on the solution as a whole. The pure trimer content of the solid amounted to 52%.

After hydrolysis of the isocyanate groups, the content of aromatic and aliphatic amine functions was determined by titrimetry and only 2.9% of all the amine functions were aromatic in character.

EXAMPLE 3

3.2 g of 2-(N,N-dimethylaminomethyl)-4-nonylphenol were added under nitrogen to 1000 g (3.7 moles) of diisocyanate B.

A slightly exothermic reaction began spontaneously, as a result of which the temperature rose slowly to 40°–45° C. After a reaction time of 3 hours, during which the temperature remained constant at 40°–45° C. in the absence of external cooling or heating and the NCO-content fell to 27.2%, the reaction was terminated by the addition of 2.2 g of toluene sulfonic acid methyl ester and heating for 1 hour to 100° C. (degree of trimerization: 10%).

According to analysis by gel chromatography, the monomer content of the product thus produced amounted to 74%, while the pure trimer content amounted to 27% and the content of compounds containing two isocyanurate units amounted to 1.2%. Compounds of higher molecular weight could not be detected.

Separation of the excess diisocyanate by thin-layer distillation (wall temperature: 200° C., pressure: 0.5 mbar) left a pale yellow, clear and solid resin, of which a 60% solution in ethyl glycol acetate had an NCO-content of 8.9%, a viscosity—as measured at 25° C.—of 910 mPas and a monomer content—as determined by gel chromatography—of less than 1.0%.

EXAMPLE 4

150 g (0.56 mole) of diisocyanate C were mixed under nitrogen with 100 g of ethyl glycol acetate, followed by the addition with stirring of 0.04 g of 1,4-diazabicyclo-(2,2,2)-octane and 1.9 g of 2-(N,N-dimethylaminomethyl)-4-nonylphenol A slightly exothermic reaction began, as a result of which the temperature rose to 40° C. After stirring for 24 hours at 40° C., the reaction was terminated at an NCO-content of 8.3% by the addition of 1.4 g of toluene sulfonic acid methyl ester, followed by heating for 1 hour to 80° C. (degree of trimerization: 55%).

The pale yellow product obtained had an NCO-content of 8.3% and a viscosity at 25° C. of 1800 mPas.

According to analysis by gel chromatography, the solution had a monomer content of 1.8%, while the pure trimer content of the solid amounted to 51%.

EXAMPLE 5

150 g (0.53 mole) of diisocyanate D were mixed with 100 g of ethyl glycol acetate, followed by the addition with stirring of 0.04 g of 1,4-diazabicyclo-(2,2,2)-octane and 1.8 g of 2-(N,N-dimethylaminomethyl)-4-nonylphenol.

A mildly exothermic reaction began, as a result of which the temperature rose slowly to around 40° C. After stirring for 72 hours at 40° C., the NCO-content had fallen to 7.6% and the reaction was terminated by the addition of 1.4 g of toluene sulfonic acid methyl ester and subsequent heating for 1 hour to 100° C. (degree of trimerization: 57%).

The pale yellow solution obtained, of which the NCO-content amounted to 7.6% after termination, had a viscosity at 25° C. of 1200 mPas and a monomer content, according to analysis by gel chromatography, of 1.3%, based on the solution. The pure trimer content of the solid amounted to 43%.

EXAMPLE 6

150 g (0.53 mole) of diisocyanate E were dissolved in 100 g of ethyl glycol acetate and the resulting solution reacted in the same way as described in Example 5.

After stirring for 8 hours at 40° C., the NCO-content had fallen to 7.8% and, after standing for another 20 hours at room temperature, to 7.5%.

The reaction was terminated by the addition of 1.4 g of toluene sulfonic acid methyl ester and subsequent heating for 1 hour to 100° C. (degree of trimerization: 58%).

After termination, the substantially colorless, clear solution obtained had an NCO-content of 7.4% and a viscosity of 1200 mPas (25° C.). According to analysis by gel chromatography, the monomer content amounted to 0.7%, based on the solution, and the pure trimer content of the solid amounted to 44%.

EXAMPLE 7

100 g (0.35 mole) of diisocyanate F were mixed under nitrogen with 100 g of ethyl glycol acetate, followed by the addition with stirring of 0.05 g of 1,4-diazabicyclo-(2,2,2)-octane and 1.25 g of 2-(N,N-dimethylaminomethyl)-4-nonylphenol.

The reaction mixture was then heated to 40° C. since the NCO-content had only fallen to 11.6% after stirring for 24 hours, another 2.5 g of 2-(N,N-dimethylaminomethyl)-4-nonyl phenol were added and the reaction mixture stirred at 40° C. for another 48 hours. Trimerization was then terminated at an NCO-content now amounting to 6.5% by the addition of 1.5 g of toluene sulfonic acid methyl ester and subsequent heating for 1 hour to 100° C. (degree of trimerization: 55%).

The resulting product was pale yellow in color and had an NCO-content of 5.9% and a viscosity of 320 mPas at 25° C. According to analysis by gel chromatography, the monomer content amounted to 1.4% by weight, based on the solution, and the pure trimer content of the solid amounted to 37%.

EXAMPLE 8

100 g (0.34 mole) of diisocyanate K were mixed under nitrogen with 67 g of ethyl glycol acetate, followed by the addition with stirring of 0.4 g of 1,4-diazabicyclo-(2,2,2)-octane and 4.1 g of a 0.2-molar solution of complexed potassium acetate (potassium acetate+ crown ether) (18)-crown-6, molar ratio 1:1) in diethylene glycol monomethyl ether. The reaction which began spontaneously produced a rapid increase in temperature to 60° C. The reaction mixture was stirred at that temperature for 25 hours, by which time the NCO-content amounted to 9.1%, after which the reaction was terminated by the addition of 1.2 g of perfluorobutane sulfonic acid and subsequent heating for 1 hour to 100° C. (degree of trimerization: 45%).

The resulting, slightly cloudy product was yellowish in color and had an NCO-content of 9.0% and a viscosity at 25° C. of 90 mPas. According to analysis by gel chromatography, the monomer content amounted to 15%, based on the solution, and the pure trimer content, based on solids, amounted to 22%.

EXAMPLE 9

100 g of diisocyanate K were mixed under nitrogen with 67 g of xylene, followed by the addition with stirring of 0.4 g of 1,4-diazabicyclo-(2,2,2)-octane and 3.5 g of a 25% solution of tetrabutyl ammonium hydroxide in methanol.

As a result of the mildly exothermic reaction which began immediately, the temperature rose to around 60° C. in 20 minutes. During the following 2-hour reaction, throughout which the temperature was kept constant at 60° C., the NCO-content fell to 6%. The reaction was then terminated by the addition of 1.8 g of 2-ethyl hexanoic acid and subsequent heating for 1 hour to 100° C. (degree of trimerization: 64%).

A clear, substantially colorless product having an NCO-content of 5.6% and a viscosity of 3500 mPas (25° C.) was obtained. The monomer content, as determined by gel chromatography, amounted to 1.9%, based on the solution, and the pure trimer content, based on solids, amounted to 13%.

After hydrolysis of the isocyanate groups, the content of aromatically and aliphatically bound amine groups was determined by titrimetry and 25 to 30% of all the amine groups were aromatic in character.

EXAMPLE 10

17.4 g of 2-(N,N-dimethylaminomethyl)-4-nonyl phenol and 0.7 g of 1,4-diazabicyclo-(2,2,2)-octane were added under nitrogen to 1500 g (5.0 moles) of diisocyanate K. A slightly exothermic reaction began immediately, as a result of which the temperature rose slowly to 30°-40° C.

After a reaction time of 15 hours, during which the temperature was kept constant at 40° C. by gentle heating, the reaction was terminated at an NCO-content of 23% by the addition of 16 g of toluene sulfonic acid methyl ester and subsequent heating for 1 hour to 100° C. (degree of trimerization: 17%).

The excess diisocyanate was then removed by thin-layer distillation (wall temperature: 205° C., pressure: 0.5 mbar) and the pale-yellow resin obtained, which had a melting point in the range from 155° to 167° C., was taken up in ethyl glycol acetate. The 60% solution obtained had an NCO-content of 7.5%, a viscosity—as measured at 25° C.—of 420 mPas and a monomer content—as determined by gel chromatography—of 1.8%. The pure trimer content, based on solids, amounted to 60%.

EXAMPLE 11

100 g of diisocyanate G were mixed under nitrogen with 67 g of ethyl glycol acetate, followed by the addition with stirring of 3.3 g of 2-(N,N-dimethylaminomethyl)-4-nonyl phenol and 5 g of a 2% solution of 1,4-diazabicyclo-(2,2,2)-octane in ethyl glycol acetate. Since the NCO-content had only fallen to 12.6% after stirring for 18 hours at 40° C., the reaction was recatalyzed by the addition of 3 ml of a 0.2-molar solution of complexed potassium acetate (potassium acetate + crown ether (18)-crown-6, molar ratio 1:1) in diethylene glycol monomethyl ether.

After stirring for another 15 hours at 40° C., the NCO-content had fallen to 7.4%. 2 g of toluene sulfonic acid methyl ester were then added and the reaction mixture was heated for 1 hour to 100° C. (degree of trimerization: 51%).

The resulting end product was slightly cloudy and was yellow in color. Its NCO-content amounted to 7.3% and its monomer content, as determined by high pressure liquid chromatography, amounted to 10%. Its viscosity at 25° C. measured approximately 600 mPas.

EXAMPLE 12

100 g of diisocyanate H were mixed under nitrogen with 25 g of ethyl glycol acetate and 40 g of xylene, followed by the addition of 0.2 g of 1,4-diazabicyclo-(2,2,2)-octane and 2 ml of a 0.2-molar solution of complexed potassium acetate (potassium acetate + crown ether (18)-crown-6, molar ratio 1:1) in diethylene glycol monomethyl ether. Since the NCO-content had only fallen to 10.3% after stirring for 30 hours at 60° C., the reaction was recatalyzed by the addition of 1.7 g of 2-(N,N-dimethylaminomethyl)-4-nonyl phenol and the reaction mixture stirred for another 90 hours at 60° C. The reaction was terminated at an NCO-content of 5.6% by the addition of 0.33 g of toluene sulfonic acid methyl ester and by subsequent heating for 1 hour to 100° C. (degree of trimerization: 62%).

The resulting product was slightly cloudy and pale yellow in color, its NCO-content amounted to 5.6% and its monomer content—as determined by gel chromatography—amounted to 9%, based on the solution. Its viscosity at 25° C. measured approximately 900 mPas.

EXAMPLE 13

2000 g (7.4 moles) of diisocyanate B were dissolved in 1240 g of ethyl glycol acetate and, following the addition of 24 g of 2-(N,N-dimethylaminomethyl)-4-nonyl phenol and 0.6 g of 1,4-diazabicyclo-(2,2,2)-octane, the resulting solution was reacted as in Example 2 to form the isocyanato-isocyanurate. After the NCO-content had fallen to 8.1%, 18 g of toluene sulfonic acid methyl ester were added and the reaction mixture was subsequently heated for 1 hour to 100° C. (degree of trimerization: 56%).

The pale yellow solution obtained (iodine color number according to DIN 6162: 1-2) had an NCO-content of 8.0% and a viscosity—as measured at 25° C.—of 2400 mPas. According to analysis by gel chromatography, the monomer content amounted to less than 0.5%.

EXAMPLE 14

600 g of the trimer solution prepared in Example 13 were stirred by means of a high-performance stirrer into 6 liters of ligroin. A finely particulate solid precipitated and was filtered under suction in a nitrogen atmosphere and subsequently dried at 50° C./100 mbar.

The pure white product obtained (350 g) had an NCO-content of 12.8% and a melting range of 120°-170° C. and was still free-flowing, even after storage for several weeks at 50° C.

EXAMPLE 15

1000 g of the trimer solution prepared in Example 13 were heated under nitrogen to 80° C., followed by the addition over a period of 15 minutes of a solution of 218 g of ε-caprolactam in 250 g of ethyl glycol acetate.

After stirring for 24 hours at 80° C., the NCO-content had fallen to less than 0.2%. The viscosity of the pale-yellow, clear product obtained amounted to 5700 mPas at 25° C.

800 g of a solvent-free product having an NCO-content of 0.15% and a melting range of 150° to 190° C. were obtained by stirring with ligroin and drying at 50° C./100 mbar. The product, which accumulated in the form of a white powder, was still free-flowing after storage for several weeks at 50° C.

EXAMPLE 16

500 g of the trimer solution prepared in Example 13 were heated under nitrogen to 40° C., followed by the addition over a period of 30 minutes of a solution of 76 g of butanone oxime in 100 g of ethyl glycol acetate.

After stirring for 3 hours at 40° C., the NCO-content had fallen to less than 0.1%. The highly viscous solution obtained was then stirred into 5 liters of ligroin and the precipitated, finely particulate solid was filtered off under suction. The white powder, obtained in a quantity of 350 g after drying at 50° C./100 mbar, had an NCO-content of less than 0.1% and a melting range of 100° to 140° C. and was still free-flowing after storage for several weeks at 50° C.

APPLICATION EXAMPLES

The isocyanato-isocyanurates produced from diisocyanate B in accordance with Examples 13 and 14 were reacted using hydroxyl-containing polyester resins of the type commonly encountered in lacquer technology to form ready-to-use lacquers of which the lacquer properties were then determined. Corresponding lacquers were produced using conventional isocyanato-isocyanurates and tested for comparison purposes. The following starting materials were used in these tests:

Polyester resin I: a polyester produced from 29,8 parts by weight of peanut fatty acid 32,0 parts by weight of trimethylol propane and 8,8 parts by weight of triethylene glycol and having a hydroxyl group content of 3,1%(75% solution in xylene).

Polyester resin II: a polyester procuded from 66,6 parts by weight of terephthalic acid, 38,2 parts by weight of neopentyl glycol, 1,0 parts by weight of 1,6-dihydroxy hexane and 0,74 parts by weight of trimethylol propane and having a hydroxyl group content of 1,5%.

Polyester resin III: polyester resin II containing an addition of 10% of a commercially available polyacrylate-based levelling agent (Acronal 4 F., a product of BASF AG, Ludwigshafen).

Polyisocyanate I: a mixed trimer of 2,4-diisocyanato toluene and 1,6-diisocyanato hexane (Desmodur HL, a product of BAYER AG, Leverkusen) having a residual monomer content of less than 0.7% by weight and an NCO-content of 10.4% (60% solution in butyl acetate).

Polyisocyanate II: an ε-caprolactam-blocked adduct of diisocyanato-toluene (65% of 2,4-and 35% of 2,6-isomer) with diethylene glycol containing 12.5% of blocked NCO-groups (expressed as NCO).

EXAMPLE 17

69.7 parts by weight of the trimer solution produced in accordance with Example 13, together with 75.3 parts by weight of polyester resin I and 17.0 parts by weight of a 10% solution of cellulose acetobutyrate in butyl acetate, were dissolved in 86.3 parts by weight of a solvent mixture containing butyl acetate, ethyl acetate, toluene and ethyl glycol acetate (27:20.2:27:12.1). 1.7 parts by weight of a commercially available polyether siloxane-based levelling agent (10% solution in toluene, Baysilon-ÖL, a product of BAYER AG, Leverkusen) were added to the resulting solution. In a comparison test, a similar lacquer solution was prepared using 84.9 parts by weight of polyisocyanate solution I.

Films prepared with these ready-to-use lacquers (layer thickness after drying: approximately 50 μm) were tested for light stability in accordance with DIN 53 389 (Xeno test 150). The results obtained are shown in the following Table.

|  | According to the invention | Comparison |
| --- | --- | --- |
| Xeno test 150 after 0 h | 1.0 | 1.3 |
| Xeno test 150 after 50 h | 1.0 | 1.6 |
| Xeno test 150 after 100 h | 1.1 | 2.0 |
| Xeno test 150 after 150 h | 1.3 | 2.1 |
| Xeno test 150 after 200 h | 1.4 | 2.4 |

The figures (scale of 0 to 5 according to DIN 43 230), which have higher values with increasing discoloration, clearly reflect the higher light stability of the lacquer film produced with the trimer according to the invention.

EXAMPLE 18

15.3 parts by weight of the solvent-free trimer obtained in Example 14 were homogeneously mixed with 45.1 parts by weight of polyester resin II, 6.6 parts by weight of polyester resin III and 33 parts by weight of a commercially available pigment based on titanium dioxide in a screw reactor at 100° to 120° C. and the resulting mixture was subsequently extruded.

Subsequent grinding produced a fine, powder-form product having an average particle size of 50 μm. This material was still free flowing after storage for 4 weeks at 50° C.

In a comparison test, a similar product was produced using 15.3 parts by weight of polyisocyanate II.

Performance testing, in which the above products were applied by electrostatic powder coating to 0.8 mm thick iron plates and subsequently stoved for 30 minutes at 180° C., produced the following results:

|  | According to the invention | Comparison |
| --- | --- | --- |
| Layer thickness in μm | 56–63 | 71–76 |
| Gloss (60° C.) according to Gardner | 69 | 63 |
| Cross hatching according to DIN 53 151 | o/o | o/o |
| Erichsen indentation in mm according to DIN 53 156 | 10 | 10 |
| rev. Impact values in cm/kg (ball weight: 1 kg, ball diameter: 12.7 mm) | 140 | 150 |
| Whiteness according to Berger |  |  |
| untreated | 75.0 | 65.6 |
| after 15 minutes at 200° C. | 70.4 | 62.7 |
| after another 20 minutes at 220° C. | 56.5 | 47.5 |

In order to determine gloss retention after weathering, aluminum plates were coated with the two powder lacquers mentioned and, after stoving, were subjected to the "weather-o-meter" test according to DIN 67 530 T. The results are shown in the following Table.

| Reflection (60°, 20°) according to Gardner | According to the invention | Comparison |
| --- | --- | --- |
| after 0 hours | 50 (20°) = 80 (60°) | 64 (60°) |
| after 100 hours | 50 (20°) 80 (60°) | 62 (60°) |
| after 200 hours | 50 (20°) 80 (60°) | 49 (60°) |
| after 300 hours | 69 (60°) | 24 (60°) |
| after 400 hours | 55 (60°) | 16 (60°) |
| after 600 hours | 30 (60°) | 13 (60°) |

For otherwise equally or similarly favorable values, the lacquer film based on the trimer according to the invention shows distinctly better properties than the corresponding film based on the comparison isocyanate II, particularly in regard to whiteness under thermal load and in regard to gloss retention after weathering.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Isocyanato-isocyanurates corresponding to the formula

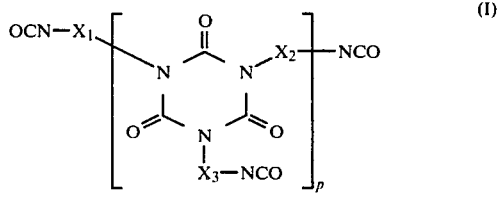

in which $X_1$, $X_2$ and $X_3$ may be the same or different and represent radicals corresponding to the formula

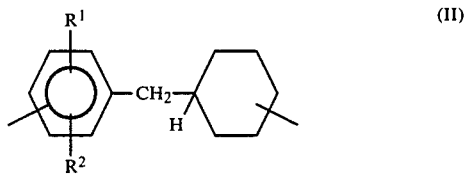

wherein $R^1$ represents hydrogen, $R^2$ represents a $C_1$-$C_3$ alkyl group and p is a whole or (on a statistical average) fractional number of from 1 to 5.

2. The isocyanato-isocyanurates of claim 1 wherein from about 90 to 100% of the isocyanate groups, based on all the isocyanate groups, are cycloaliphatically bound isocyanate groups.

3. The isocyanato-isocyanurates of claim 1 wherein at least about 90% by weight of the isocyanato-isocyanurates are compounds corresponding to formula (I) in which p is a whole or (on a statistical average) fractional number of from 1 to 3.

* * * * *